US009226902B2

(12) United States Patent
Tang

(10) Patent No.: US 9,226,902 B2
(45) Date of Patent: Jan. 5, 2016

(54) STABILIZED TRANSDERMAL DRUG DELIVERY SYSTEM

(75) Inventor: Jiashang Tang, Morgantown, WV (US)

(73) Assignee: Mylan Technologies Inc., St. Albans, VT (US)

(*) Notice: Subject to any disclaimer, the term of this patent is extended or adjusted under 35 U.S.C. 154(b) by 677 days.

(21) Appl. No.: 12/475,390

(22) Filed: May 29, 2009

(65) Prior Publication Data
US 2009/0299304 A1 Dec. 3, 2009

Related U.S. Application Data

(60) Provisional application No. 61/057,455, filed on May 30, 2008.

(51) Int. Cl.
A61F 13/02 (2006.01)
A61K 9/70 (2006.01)

(52) U.S. Cl.
CPC ............. A61K 9/7061 (2013.01); A61K 9/7069 (2013.01); A61K 9/7092 (2013.01); Y10T 156/10 (2015.01)

(58) Field of Classification Search
CPC . A61K 9/7061; A61K 9/7069; A61K 9/7092; Y10T 156/10
See application file for complete search history.

(56) References Cited

U.S. PATENT DOCUMENTS

| 4,409,206 | A |   | 10/1983 | Stricker |
| 4,490,322 | A |   | 12/1984 | Zierenberg |
| 4,797,284 | A |   | 1/1989 | Loper et al. |
| 4,832,953 | A |   | 5/1989 | Campbell et al. |
| 4,880,633 | A |   | 11/1989 | Loper et al. |
| 5,164,190 | A |   | 11/1992 | Patel et al. |
| 5,352,457 | A |   | 10/1994 | Jenkins |
| 5,494,680 | A | * | 2/1996 | Peterson ................. 424/448 |
| 5,662,928 | A |   | 9/1997 | Braun |
| 5,869,089 | A |   | 2/1999 | Wu |
| 5,906,830 | A |   | 5/1999 | Farinas et al. |
| 6,153,216 | A |   | 11/2000 | Cordes et al. |
| 6,156,335 | A |   | 12/2000 | Rovati et al. |
| 6,238,700 | B1 |   | 5/2001 | Dohner et al. |
| 6,569,448 | B1 |   | 5/2003 | Dohner et al. |
| 6,623,763 | B2 |   | 9/2003 | Asmussen et al. |
| 6,902,741 | B1 | * | 6/2005 | Grawe et al. ............ 424/448 |
| 2001/0009673 | A1 |   | 7/2001 | Lipp et al. |
| 2004/0018241 | A1 | * | 1/2004 | Houze et al. ............ 424/486 |
| 2004/0057985 | A1 |   | 3/2004 | Bracht |
| 2004/0081683 | A1 |   | 4/2004 | Schacht et al. |
| 2005/0064022 | A1 |   | 3/2005 | Tavares et al. |
| 2005/0175678 | A1 |   | 8/2005 | Breitenbach |
| 2006/0099242 | A1 |   | 5/2006 | Garbe et al. |
| 2006/0188558 | A1 |   | 8/2006 | Jackson et al. |
| 2008/0226698 | A1 | * | 9/2008 | Tang et al. ............ 424/448 |
| 2009/0048232 | A1 | * | 2/2009 | Ciccocioppo ........... 514/214.02 |

FOREIGN PATENT DOCUMENTS

| EP | 1671626 A1 | 6/2006 |
| JP | S60-169414 | 9/1985 |
| JP | 2014-505714 A | 3/2014 |
| WO | 95/18603 A1 | 7/1995 |
| WO | WO 2006/091442 | 8/2006 |
| WO | WO 2007/077741 | 7/2007 |
| WO | 2008/115371 A2 | 9/2008 |
| WO | 2012/110469 A1 | 8/2012 |

OTHER PUBLICATIONS

Office Action mailed Oct. 24, 2013, which issued during the prosecution of Japanese Application No. 2011-511876, which corresponds to the present application.
Decision of Rejection, mailed Jul. 17, 2014, which issued during the prosecution of Japanese Patent Application No. 2011-511876, which corresponds to the present application.
Taylor L S et al., "Spectroscopic Characterization of Interactions Between PVP and Indomethacin in Amorphous Molecular Dispersions," Pharmaceutical Research, Kluwer Academic Publishers, New York, NY, US, vol. 14, No. 12, Dec. 1, 1997, pp. 1691-1698, XP000905065.
Communication pursuant to Article 94(3) EPC, dated Jul. 1, 2014, which issued during the prosecution of EP Patent Application No. 09 770 655.0, which corresponds to the present application.
Examination Report, dated Jun. 24, 2014, which issued during the prosecution of Australian Patent Application No. 2009262871, which corresponds to the present application.

* cited by examiner

Primary Examiner — Suzanne Ziska
(74) Attorney, Agent, or Firm — Blank Rome, LLP

(57) ABSTRACT

A solid dispersion transdermal drug delivery system comprising a therapeutic agent in a stable amorphous form and a combination polymeric stabilizing and dispersing agent having a hydrogen bond-forming functional group, and a method of manufacturing these systems is provided. The weight ratio of the combination polymeric stabilizing and dispersing agent to the therapeutic agent is also disclosed.

25 Claims, 2 Drawing Sheets

10 = Device (3-layers)
11 = Backing Layer
12 = Adhesive Layer
13 = Protective Release Liner 20 = Device (4-layers)
21 = Backing Layer
22 = Drug Reservoir Layer
23 = Skin Contact Layer
24 = Protective Release Liner 30 = Device (5-layers)
31 = Backing Layer
32 = Drug Reservoir Layer
33 = Membrane, woven mesh, or non-woven
34 = Skin Contact Layer

STABILIZED TRANSDERMAL DRUG DELIVERY SYSTEM

This application claims priority to U.S. Provisional Application 61/057,455, which was filed May 30, 2008, and is hereby incorporated by reference in its entirety.

FIELD OF THE INVENTION

The present invention relates to a solid dispersion transdermal drug delivery system comprising a therapeutic agent in a stable amorphous form and a polymeric stabilizer capable of hydrogen bonding with the therapeutic agent, and to a method of manufacturing these systems. Further, the present invention relates to the importance of the weight ratio of the polymeric stabilizer to the therapeutic agent in stabilizing the therapeutic agent.

BACKGROUND OF THE INVENTION

Transdermal drug delivery, delivery of drugs through the skin, provides many advantages. Primarily, it is a comfortable, convenient and non-invasive way of administering drugs. Drugs delivered transdermally directly enter subdermal blood vessels, and are transported to the target site via by-passing the first-pass liver metabolism and decomposition. This method allows for high drug bioavailability. The system requires a relatively small amount of drug and can be an effective method for sustained drug delivery, allowing for a reduced frequency of administration. Moreover, such a means of delivery provides uninterrupted therapy and a higher degree of control over drug concentrations in the blood. These characteristics help avoid side effects caused by temporarily high blood concentrations of drugs which accompany administration of oral dosage forms and injections.

The outer layer of the skin called the stratum corneum, however, forms a barrier to drug absorption for almost all compounds and often prevents the delivery of an effective amount of the drug. Due to the hydrophobic nature of the stratum corneum, absorption of the hydrophilic salts of drugs is especially difficult. Large molecules and extremely hydrophobic drugs also have difficulty being absorbed through the skin.

Chemical enhancers are commonly used to overcome the stratum corneum barrier. These enhancers, however, can introduce side effects such as skin irritation and formulation incompatibility and often still can not increase drug absorption sufficiently to meet the drug's therapeutic dose requirement.

Additionally, physical means are a common method used to overcome the stratum corneum barrier function. These means include iontophoresis, electroporation, sonophoresis, and skin micro abrasion.

U.S. Pat. No. 4,409,206 discloses a preparation in the form of a polyacrylate film with an amorphous active pharmaceutical ingredient embedded therein.

United States Publication No. 2005/0064022 describes a terazosin transdermal device and methods of use. The publication discloses the preparation of terazosin in amorphous form by spray drying, roller drying and freeze drying prior to incorporation into the transdermal delivery device. More specifically, the publication discloses a transdermal therapeutic system for the administration of amorphous terazosin to the skin, comprising a backing layer, a pressure-sensitive adhesive reservoir layer and/or a matrix layer, and optionally a removable protective layer.

United States Publication No. 2005/0175678 is directed to a polymer matrix suitable for the transdermal administration of rotigotine and a method of preparing the same. The polymer matrix contains a supersaturated amount of a rotigotine base such that the portion of the rotigotine that is not dissolved in the matrix polymeric adhesive is dispersed in the adhesive matrix as amorphous particles. The publication further discloses that the matrix adhesive may be a component of a system for transdermal administration of rotigotine, wherein the system can have components such as a protective layer, a backing layer, further polymeric adhesive layers, and/or a membrane which controls the release of the rotigotine.

U.S. Pat. No. 6,902,741 is directed to a transdermal system which includes a sex hormone-containing adhesive matrix, containing inclusions of sex hormone in a hydrophilic non-crosslinked polymer. The active sex hormone contained in the inclusions is preferably amorphous to an extent of more than 50% by weight of the active substance. The active sex hormone-containing laminate is characterized in that the active sex hormone inclusions are contained in the adhesive matrix in dissolved or dispersed form and that the active sex hormone inclusions are pre-prepared prior to incorporation to the adhesive matrix. Thus the process requires a step of pre-preparation of the active hormone inclusion, followed by another step of incorporating the inclusions to an adhesive matrix polymer solution.

Various methods of manufacturing transdermal systems in which the drug is supersaturated are known. U.S. Pat. Nos. 4,409,206, 4,490,322, 4,797,284, 4,880,633, 5,352,457 5,869,089, 5,906,830, 6,153,216, 6,156,335, and 6,623,763 describe methods of manufacturing transdermal systems. U.S. Pat. No. 4,490,332 discloses a method of manufacturing a polyacrylate film for long term transdermal administration by forming a solution of a pharmaceutical and a freeze-dried latex polyacrylate copolymer in a solvent. U.S. Pat. No. 5,906,830 discloses a method of manufacturing a supersaturated transdermal system comprising heating a mixture of undissolved drug and reservoir matrix material to a predetermined temperature, followed by cooling.

Scopolamine is a difficult molecule to administer transdermally as the molecule recrystallizes in both laminate and patch delivery systems. As this recrystallization occurs, the delivery rate is reduced. Several U.S. patents (U.S. Pat. Nos. 4,832,953, 5,662,928, 6,569,448, 6,238,700) describe an annealing method to anneal laminates and patches for removal or prevention of formation of crystalline scopolamine or their hydrates. These processes are tedious, complex and costly.

Oxybutynin is also a troublesome molecule for transdermal delivery. U.S. Pat. No. 5,164,190 discloses transdermal administration of hydrophobic drugs via a diffusion mechanism in which the drug is dissolved in a carrier at concentrations between 20% and 80% of saturation concentration. U.S. Patent Application No. 2004/0057985 discloses a transdermal system wherein a matrix layer comprises two phases which are immiscible with each other, namely an inner phase and an outer phase.

U.S. Patent Application No. 2004/0081683 discloses a transdermal system containing a self-adhesive matrix consisting of an adhesive polymer and an amine functional drug including oxybutynin and is free of particles that absorb salts of amine functional drugs.

Naltrexone is poorly absorbed through the skin and therefore prodrugs have been developed to enhance the skin absorption. The absorption rate of the prodrugs, however, is still insufficient to achieve therapeutic dosages.

Testosterone is also poorly absorbed from the skin even in the presence of a high level of enhancers.

Although the required therapeutic dose is low, the transdermal delivery rate of crystalline estradiol often can not achieve the therapeutic level.

Thus there remains a need for a stable transdermal system which can improve the absorption rate through the skin for various therapeutic agents.

SUMMARY OF THE INVENTION

In accordance with the present invention, a solid dispersion transdermal drug delivery system is provided which has an improved stability and absorption rate from the skin for various therapeutic agents. The transdermal drug delivery system of the invention, includes a stable amorphous form of a therapeutic agent, and a polymeric stabilizer which is also a dispersant capable of forming hydrogen bonding with the therapeutic agent. The transdermal drug delivery system of the invention is further characterized by the long-term stability of the therapeutic agent dependent upon the ratio of the therapeutic agent to the polymeric stabilizer.

The transdermal drug delivery system of the present invention further comprises at least three layers: a backing film, an adhesive layer, and a protective release liner. The adhesive layer comprises an adhesive, a therapeutic agent in amorphous form, and a combination polymeric stabilizing and dispersing agent comprising a hydrogen bond-forming functional group and a protective release liner.

The invention is particularly adapted to transdermal drug delivery systems wherein the therapeutic agent may be, for example, (i) scopolamine, oxybutynin, naltrexone, testosterone, estradiol, rotigotine, fentanyl, ethinyl estradiol, or norelgestral (ii) any pharmaceutically acceptable salts of any of (i), or any combination of any of (i), (ii), or (i) and (ii).

Another embodiment of the invention includes a fourth layer. This second adhesive layer, or skin contact adhesive layer, is also comprised of an adhesive, a therapeutic agent in amorphous form, and combination polymeric stabilizing and dispersing agent comprising a hydrogen bond-forming functional group. The second adhesive layer resides between the first adhesive layer (a drug reservoir adhesive layer) and the protective release liner. The second adhesive may be the same as or different from the first adhesive, and the second therapeutic agent in amorphous form may be the same as or different from the first therapeutic agent. The second combination polymeric stabilizing and dispersing agent may be the same as or different from said first combination polymeric stabilizing and dispersing agent.

Another embodiment of the invention includes a fifth layer. The fifth layer comprises a membrane which resides between the drug reservoir adhesive layer and the skin contact adhesive layer.

In another embodiment of the invention, the adhesive layer (the drug reservoir adhesive layer and/or the skin contact adhesive layer) may additionally include a skin penetration enhancer, tackifier, and/or cohesive promoter.

In accordance with the present invention, the amorphous form of a therapeutic agent which contains at least one hydrogen bond-forming group remains stable for a long period of time when it is dispersed within a polymeric material matrix which also contains at least one hydrogen bond-forming group. The hydrogen bond association between the molecules of the therapeutic agent and the polymeric material also provides additional dispersion capability. The greater dispersion capability is compared to an identical drug delivery device that does not have a polymeric stabilizing/dispersing agent. The greater dispersion capacity may include, for example, an increased amount of therapeutic agent dispersed in the polymeric material or greater uniformity of the therapeutic agent dispersed through the polymeric material as compared to a dispersion without hydrogen bonding.

In accordance with the present invention, the stability of the therapeutic agent is increased if the weight ratio of the polymeric material containing at least one hydrogen bond-forming group to the therapeutic agent is at least 0.5.

In accordance with the present invention, the stability of the therapeutic agent in the transdermal drug delivery system is characterized by the therapeutic agent's ability to remain amorphous over time without forming crystals.

In one aspect of the present invention, at least 95% of said therapeutic agent is in amorphous form after storage at room temperature for at least six months. In another aspect of the present invention, at least 99% of said therapeutic agent is in amorphous form after storage at room temperature for at least six months. In yet another aspect of the present invention, at least 99% of said therapeutic agent is in amorphous form after storage at room temperature for at least 18 months.

In another aspect of the present invention, the therapeutic agent has a skin absorption rate which is increased by at least 25% compared to the skin absorption rate of the therapeutic agent in an identical transdermal drug delivery without said polymeric stabilizing/dispersing agent. In another aspect of the present invention, the absorption rate is increased by at least 50%. In another aspect of the present invention, the skin absorption rate is increased by at least 75%.

Additionally, if the therapeutic agent has a low glass transition temperature, the weight ratio of the polymeric material to the amorphous form of a therapeutic agent required to disperse the amorphous form of the therapeutic agent is 2 or greater. In one aspect of the present invention, the low glass transition temperature is less than 50° C. In another aspect of the present invention, the low glass transition temperature is less than 40° C.

The ratio of the weight of the polymeric material to the amorphous form of a therapeutic agent required to stabilize the amorphous form of a therapeutic agent with a high glass transition temperature is 0.5 or greater. In one aspect of the present invention, the high glass transition temperature is at least 60° C. In another aspect of the present invention, the high glass transition temperature is at least 70° C. In one aspect of the present invention the ratio of the weight of the polymeric material to the amorphous form of a therapeutic agent required to stabilize the amorphous form of a therapeutic agent with a high glass transition temperature is between 0.5 and 10; in another aspect, it is between 0.5 and 2.

DETAILED DESCRIPTION

The present invention is a solid dispersion transdermal drug delivery system wherein the system comprises a stable amorphous form of therapeutic agent and a polymeric stabilizer and dispersant capable of forming hydrogen bonds with the therapeutic agent. Further, the stability of the therapeutic agent of the solid dispersion transdermal drug delivery system of the invention is enhanced by the optimizing the weight ratio of the therapeutic agent to the polymeric stabilizer. It has surprisingly been found that the stability is enhanced by optimizing the weight ratio of the therapeutic agent to the polymeric stabilizer, and that such optimal ratio is dependent upon the therapeutic agent's glass transition temperature. As used herein, "transdermal" means delivery of an active pharmaceutical ingredient into and through the skin or mucosal tissue. The Figures depict several embodiments of the present invention where transdermal delivery devices are in the form of skin patches that, when applied to skin, function to transdermally deliver an active pharmaceutical ingredient.

As used herein, the term "glass transition temperature," or Tg is the temperature at which a material transitions to a glassy state from a liquid state, as measured at standard atmospheric pressure. A drug having a high glass transition temperature includes, for example, a drug having a Tg of at least 60° C. (i.e., 80° C.). A drug having a low glass transition temperature includes, for example, a drug having a Tg of less than 50° C. (i.e., 30° C.).

As used herein, the term "crystalline" and "crystallinity" of a therapeutic agent means that X-ray diffraction patterns of the therapeutic agent show ordered sharp patterns as opposed to the diffusely scattered X-rays with an amorphous compound. Alternatively, crystallinity can be measured by a technique calibrated to X-ray crystallinity, such as FT-IR, a density column, or DSC. As used herein, the term "amorphous" means that the therapeutic agent is not crystalline. See, e.g., *Remington's Pharmaceutical Sciences,* $18^{th}$ ed. page 173; *The United States Pharmacopeia,* $23^{rd}$ ed, (1995) pages 1843-1844. Typically, the amorphous therapeutic agents of this invention have a crystallinity, as measured by X-ray diffraction, of a less than about 5%, preferably less than about 2%, more preferably less than about 1%, and most preferably from about 0.5% to 0% crystallinity.

Figure 1:
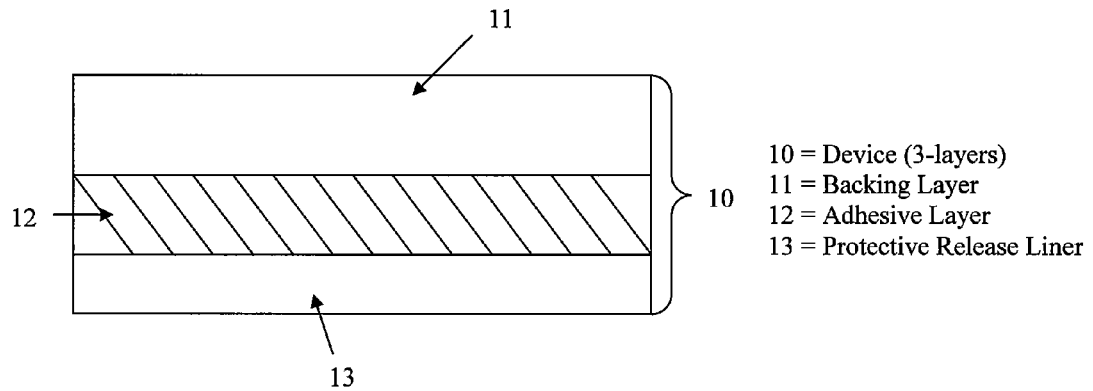
FIG. 1 is an enlarged, schematic, cross-sectional view of a three-layered transdermal delivery device of the present invention.
Figure 2:
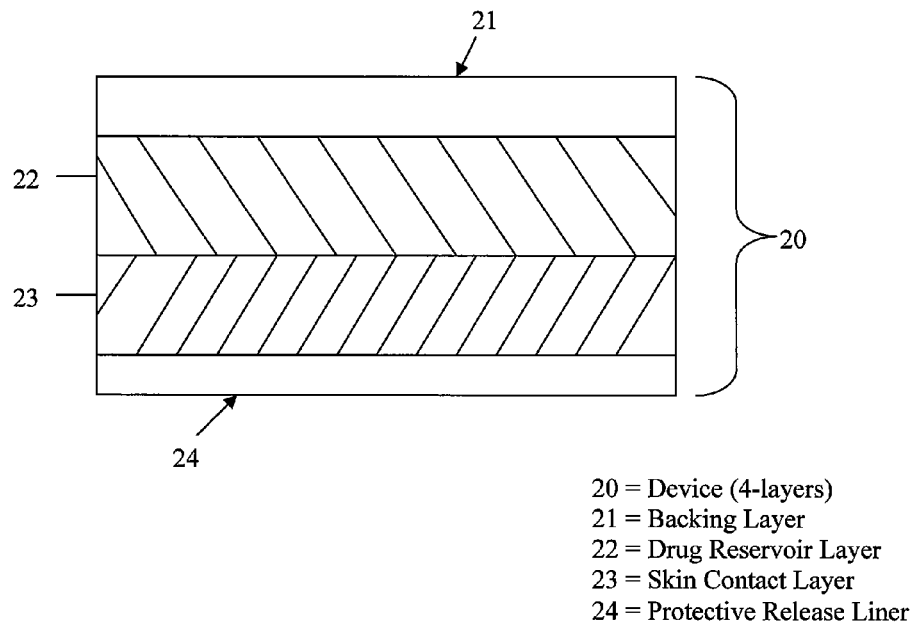
FIG. 2 is an enlarged, schematic, cross-sectional view of a four-layered transdermal delivery device of the present invention.
Figure 3:
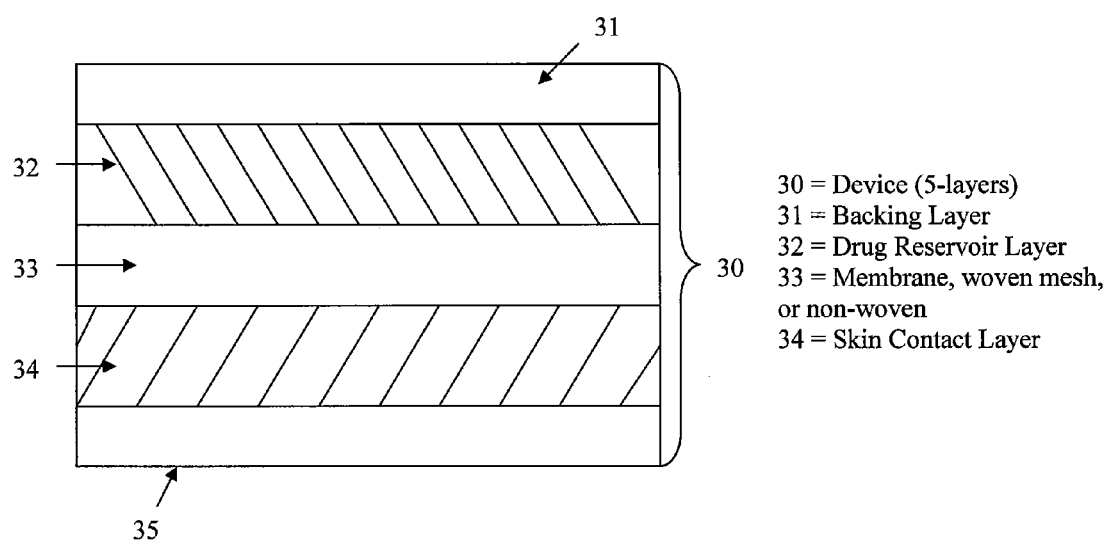
FIG. 3 is an enlarged, schematic, cross-sectional view of a five-layered transdermal delivery device of the present invention.

The solid dispersion transdermal drug delivery systems of the present invention comprise at least three layers. FIG. 1 depicts a three-layered transdermal delivery device 10 comprised of a backing layer 11, an adhesive layer 12 comprising a therapeutic agent in amorphous form, and a stabilizing agent with a hydrogen bond-forming functional group capable of hydrogen bonding with the therapeutic agent, and a protective release liner 13. FIG. 2 depicts a four-layered transdermal delivery device 20 comprised of a drug reservoir layer 22, and a skin contact layer 23, each comprising a therapeutic agent in amorphous form and a stabilizing agent with a hydrogen bond-forming functional group capable of hydrogen bonding with the therapeutic agent, a backing layer 21, and a protective release liner 24. FIG. 3 depicts a five-layered transdermal delivery device 30 comprised of a drug reservoir layer 32, and a skin contact layer 34, each comprising a therapeutic agent in amorphous form and a stabilizing agent with a hydrogen bond-forming functional group capable of hydrogen bonding with the therapeutic agent, a membrane 33 sandwiched between the drug reservoir layer 32 and skin contact layer 34, a backing layer 31, and a protective release liner 35.

The outermost layer of these solid dispersion transdermal delivery devices with respect to the skin is the backing layer, 11, 21, or 31. The backing layer is a flexible substrate which provides a barrier against migration of an active pharmaceutical ingredient away from the intended direction of drug delivery and which provides support for the device. The composition of the backing layer is not critical. Any well-known backing layer which possesses these qualities can be used in the present invention. For example, backing layers composed of the following materials can be employed: polyethylene terephthalate, nylons, polypropylenes, polyesters, polyester/ethylene-vinyl acetate, metalized polyester films, polyvinylidene chloride, metal films such as aluminum foils, polyvinylidene fluoride films, or mixtures or copolymers or laminates thereof. Specific backing layers which may be utilized include Mediflex® 1200 (available from Mylan Technologies, Inc.), Mediflex® 1501, Mediflex® 1502, Mediflex® 1503, and Scotchpak® 1109. Preferred are backing layers composed of polyethylene and polyester. Most preferred is the use of Mediflex® 1501 and Mediflex® 1200 as the backing layer.

The thickness of such backing layer is also not critical. Backing layers having a thickness ranging from about 1 mil to about 10 mils may be utilized in the practice of the present invention. Preferably, backing layers will have a thickness ranging from about 1.5 mils to about 6 mils. Most preferably, the backing layer will have a thickness of about 3 mils.

At least one adhesive layer is positioned adjacent to the backing layer on the side of the backing layer to face the patient when the device is applied. The adhesive layer comprises an adhesive, at least one therapeutic agent in amorphous form, and a stabilizing agent comprising at least one hydrogen bond-forming functional group which is capable of hydrogen bonding with the therapeutic agent. The stabilizing agent also acts as a dispersant, thereby increasing the capacity of the adhesive layer for the therapeutic agent.

The adhesive layer may be a drug reservoir adhesive layer or a skin contact adhesive layer depending on the desired structure of the system, the drug being delivered, and the release characteristics of the transdermal device. Further, the device may contain one or more of a drug reservoir adhesive layer. While the drug reservoir adhesive layer and the skin contact adhesive layer may contain the same constituent components, the amounts and/or specific types of any one component may vary between the two layers.

The size and shape of the adhesive layer is not critical and will depend upon the structure and the release characteristics of the device as well as the drug being delivered. The only limitation is that the adhesive layer may not extend beyond the backing layer.

The "adhesive material" contained in the adhesive layer may be any biocompatible polymer or polymeric material known in the art. For example, the adhesive material may be selected from silicones, natural and synthetic rubbers, polyethylene-styrene-ethylene block polymer, polystyrene-butydiene, polyisobutylene ("PIB"), polybutenes, neoprenes, polybutadienes, polyisobutenes, polyisoprenes, polysiloxanes, acrylic adhesives including cross-linked and uncross-linked acrylic copolymers, vinyl acetate adhesives, polyacrylates, ethylenevinylacetate copolymers, styrene-isoprene copolymers, polyurethanes, plasticized weight polyether block amide copolymers, plasticized styrene-rubber block copolymers, and mixtures thereof. In embodiments containing more than one adhesive layer, the type of adhesive material chosen may be the same or different for each adhesive layer. Preferably, the adhesive material is selected from the group consisting of polysiloxanes, PIB, and acrylics. Most preferably, the adhesive material is one or more polysiloxanes.

The amount of adhesive material present in the at least one adhesive layer ranges from about 30% to about 95% by weight of the adhesive layer, preferably ranging from about 35% to about 90% by weight of the adhesive layer, most preferably ranging from about 36% to about 80% by weight of the adhesive layer. In embodiments containing more than one adhesive layer, the amount of adhesive material may be the same or different for each adhesive layer.

In one preferred embodiment, the adhesive material is PIB. In another preferred embodiment, a PIB blend is used comprising a low molecular weight PIB (about 25,000 to about 50,000 viscosity average molecular weight) and a high molecular weight PIB (about 700,000 to about 1,500,000 viscosity average molecular weight). In embodiments where a PIB blend is utilized, the ratio of low molecular weight PIB to high molecular weight PIB ranges from about 95:5 to about 55:45.

The stabilizing agent contained within the adhesive layer comprises at least one hydrogen bond-forming functional group which is capable of hydrogen bonding with the therapeutic agent within the device. Non-limiting examples of hydrogen bond-forming functional groups which may be present on the stabilizing agent of the adhesive layer include hydroxyl, lower alkoxy, ether, amino, fluoro, and carbonyl.

The stabilizing agent is a compound or neutral pharmaceutical base that lowers the rate at which the therapeutic agent degrades, under environmental conditions of storage. The stabilizing agent may improve long-term stability of the therapeutic agent, wherein the term "long-term" includes at least six months. In one aspect, the stability over a time of at least 12 months is improved. In one aspect, the stability over a time of at least 18 months is improved. In one aspect, the stability over a time of at least 24 months is improved. In one embodiment, the improved stability means that less than 5% of the therapeutic agent is crystalline. In another embodiment, the improved stability means that less than 1% of the therapeutic agent is crystalline.

Non-limiting examples of the stabilizing agent used in the adhesive layer include polyvinylpyrrolidone, poly(vinylpyrrolidone-vinylacetate)copolymer, hydroxypropyl cellulose, hydroxypropyl methyl cellulose, hydroxyethyl cellulose, ethylcellulose, or a combination thereof. In preferred embodiments, the stabilizer is polyvinylpyrrolidone or poly(vinylpyrrolidone-vinylacetate)copolymer. Most preferably, the stabilizer is polyvinyl-pyrrolidone.

The amount of stabilizing agent present in the adhesive layer will vary and depend upon the identity of the stabilizing agent and the amount and identity of the adhesive material and/or the therapeutic agent. Generally, the amount of the stabilizing agent will range from about 2 to about 40 wt. % based upon the weight of the adhesive material. Preferably, it will range from about 5 to about 30 wt. % on the same basis. Most preferably, it will be present in an amount of about 5 to 20 wt. % on the same basis or from about 10% to about 20% by weight, each on the same basis.

The term "therapeutic agent" or "active pharmaceutical ingredient" is used to describe the principal active ingredient of the solid transdermal delivery device, which is a biologically active compound or mixture of compounds that has a therapeutic, prophylactic and/or physiological effect on the wearer of the device. It is present in a stable amorphous form and forms a solid dispersion with a polymer stabilizer capable of hydrogen bonding with the therapeutic agent.

Non-limiting examples of active pharmaceutical ingredients include anti-inflammatory substances, opioid receptor antagonists, anticholinergics, coronary dilators, cerebal dilators, peripheral vasodilators, alpha-adrenergic blockers, anti-infectives, psychotropics, anti-manics, stimulants, anti-histamines, decongestants, gastro-intestinal sedatives, anti-anginal drugs, vasodilators, anti-arrhythmics, anti-hypertensive drugs, vasoconstrictors, migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, anti-emetic, uterine relaxants, anti-obesity drugs, anabolic drugs, erythropoietic drugs, anti-asthmatics, bronchodilators, expectorants, mucolytics, anti-uricemic drugs and the like.

The therapeutic agent of the adhesive layer is any pharmaceutical active ingredient which contains a hydrogen bond-forming functional group. Such functional groups include, but are not limited to hydroxyl, lower alkoxy, ether, amino, fluoro, and carbonyl. Non-limiting examples of preferred therapeutic agents capable of use in the adhesive layer include scopolamine, oxybutynin, naltrexone, testosterone, estradiol, rotigotine, fentanyl, ethinyl estradiol, methylphenidate, norelgestral and piroxicam. The references to the therapeutic agents also include their salts, solvates, hydrates, prodrugs and derivative compounds of any of the foregoing. For instance, scopolamine includes the derivative compound butylscopolamine.

The amount of the therapeutic agent present in the adhesive layer will vary and depend upon, among other factors, its identity, the intended dosing of the device, the number of adhesive layers present and the amount and identity of the therapeutic agent. Generally, the amount of the therapeutic agent will range from about 0.5 to about 40 wt. % based upon the weight of the adhesive material. Preferably, it will range from about 1 to about 25 wt. % on the same basis. Most preferably, it will be present in an amount of about 5 to about 15 wt. % on the same basis.

In embodiments containing a single adhesive layer such as depicted in FIG. 1, the amount of active pharmaceutical ingredient present in the adhesive layer ranges from about 1% to about 25% by weight of the adhesive material, preferably ranging from about 5% to about 20% by weight of the adhesive material, and most preferably ranging from about 7% to about 9% by weight of the adhesive material.

In embodiments containing two adhesive layers such as depicted in FIGS. 2 and 3, the amount of active pharmaceutical ingredient in the drug reservoir adhesive layer ranges from about 1% to about 30% by weight of the drug reservoir adhesive material, preferably from about 4% to about 20% by weight of the drug reservoir adhesive material, most preferably from about 5% to about 15% by weight of the drug reservoir adhesive material. Similarly, in embodiments containing two adhesive layers such as depicted in FIGS. 2 and 3, the amount of active pharmaceutical ingredient in the skin contact adhesive layer ranges from about 0% to about 5% by weight of the skin contact adhesive material, preferably from about 2% to about 4% by weight of the skin contact adhesive material, most preferably from about 1% to about 2.5% by weight of the skin contact adhesive material.

In one embodiment, the weight ratio of the stabilizing agent to the therapeutic agent is about 0.5 or greater. The specific ratio used is dependent upon the glass transition temperature of the therapeutic agent. Those therapeutic agents with a lower glass transition temperature will remain stable in the transdermal drug delivery system when the ratio of the stabilizing agent to the therapeutic agent is 2 or greater. Such therapeutic agents with lower relative glass transition temperatures, such as scopolamine and oxybutynin, require an increased amount of stabilizing agent, by weight, to disperse and stabilize the therapeutic agent. Those therapeutic agents with a higher glass transition temperature will remain stable in the transdermal drug delivery system when the ratio of the stabilizing agent to the therapeutic agent is 0.5 or greater. Such stabilizing agents with higher relative glass transition temperatures, such as naltrexone, require a lower amount of stabilizing agent, by weight, to disperse and stabilize the therapeutic agent. Therefore, the stability of the therapeutic agent in the transdermal drug delivery system is based upon the correlation between the glass transition temperature of the therapeutic agent and weight ratio of the stabilizing agent to the therapeutic agent as inversely proportional.

In the case of scopolamine, the stabilizing agent will generally be present in an amount ranging up to about 18 wt. % based upon the weight of the adhesive material. Preferably, it will range up to about 13 wt. % on the same basis. Most preferably, it will be present in an amount of about 1 to about 12 wt. % on the same basis. Further, the weight ratio of the stabilizing agent to scopolamine is about 0.5 or greater. Preferably, the weight ratio will be about 2 or greater.

In the case of oxybutynin, the stabilizing agent will generally be present in an amount ranging up to about 25 wt. % based upon the weight of the adhesive material. Preferably, it will range up to about 20 wt. % on the same basis. Most preferably, it will be present in an amount of about 1 to about 15 wt. % on the same basis. Further, the weight ratio of the stabilizing agent to oxybutynin is about 0.5 or greater. Preferably, the weight ratio will be about 2 or greater.

In the case of naltrexone, the stabilizing agent will generally be present in an amount ranging from about 5 to about 25 wt. % based upon the weight of the adhesive material. Preferably, it will range from about 7.5 to about 20 wt. % on the same basis. Most preferably, it will be present in an amount of about 10 to about 15 wt. % on the same basis. Further, the weight ratio of the stabilizing agent to naltrexone is about 0.5 or greater. Preferably, the weight ratio of the stabilizing agent to naltrexone is between about 1 and 1.5.

In the case of testosterone, the stabilizing agent will generally be present in an amount ranging from about 5 to about 25 wt. % based upon the weight of the adhesive material. Preferably, it will range from about 5 to about 20 wt. % on the same basis. Most preferably, it will be present in an amount of about 5 and about 15 wt. % on the same basis. Further, the weight ratio of the stabilizing agent to testosterone is about 0.5 or greater.

In the case of estradiol, the stabilizing agent will generally be present in an amount ranging from about 1 to about 10 wt. % based upon the weight of the adhesive material. Preferably, it will range from about 1 to about 8 wt. % on the same basis. Most preferably, it will be present in an amount of about 1 to about 6 wt. % on the same basis. Further, the weight ratio of the stabilizing agent to estradiol is about 0.5 or greater.

In the case of rotigotine, the stabilizing agent will generally be present in an amount ranging from about 1 to about 20 wt. % based upon the weight of the adhesive material. Preferably, it will range from about 5 to about 15 wt. % on the same basis. Most preferably, it will be present in an amount of about 5 to about 10 wt. % on the same basis. Further, the weight ratio of the stabilizing agent to rotigotine is about 0.5 or greater.

In the case of fentanyl, the stabilizing agent will generally be present in an amount ranging from about 1 to about 20 wt. % based upon the weight of the adhesive material. Preferably, it will range from about 2 to about 10 wt. % on the same basis. Most preferably, it will be present in an amount of about 2 to about 5 wt. % on the same basis. Further, the weight ratio of the stabilizing agent to fentanyl is about 0.5 or greater.

In the case of ethinyl estradiol, the stabilizing agent will generally be present in an amount ranging from about 0.1 to about 10 wt. % based upon the weight of the adhesive material. Preferably, it will range from about 0.2 to about 6 wt. % on the same basis. Most preferably, it will be present in an amount of about 0.5 to about 5 wt. % on the same basis.

In the case of methylphenidate, the stabilizing agent will generally be present in an amount ranging from about 1 to about 25 wt. % based upon the weight of the adhesive material. Preferably, it will range from about 5 to about 20 wt. % on the same basis. Most preferably, it will be present in an amount of about 5 to about 15 wt. % on the same basis. Further, the weight ratio of the stabilizing agent to methylphenidate is about 0.5 or greater.

In the case of norelgestral, the stabilizing agent will generally be present in an amount ranging from about 0.5 to about 10 wt. % based upon the weight of the adhesive material. Preferably, it will range from about 0.5 to about 8 wt. % on the same basis. Most preferably, it will be present in an amount of about 0.5 to about 5 wt. % on the same basis. Further, the weight ratio of the stabilizing agent to norelgestral is about 0.5 or greater.

In the case of piroxicam, the stabilizing agent will generally be present in an amount ranging from about 0 to about 18 wt. % based upon the weight of the adhesive material. Preferably, it will range from about 0 to about 13 wt. % on the same basis. Most preferably, it will be present in an amount of about 1 to about 12 wt. % on the same basis. Further, the weight ratio of the stabilizing agent to piroxicam is about 0.5 or greater.

The adhesive layer may further comprise one or more pharmaceutically acceptable additives. Non-limiting examples of additives include cohesion-promoting additives, penetration enhancers, plasticizers, tackifiers, and similar additives. The substances suitable for this purpose are known to those skilled in the art.

The amount of additives present in the adhesive layer range from about 0.05% to about 40% by weight of the adhesive material, preferably ranging from about 1% to about 20%, and more preferably ranging from about 3% to about 20% by weight of the adhesive material. In embodiments containing more than one adhesive layer (i.e., having a first adhesive layer and at least a second adhesive layer), the amounts and/or types of additives may be the same or different for each adhesive layer.

Non-limiting examples of cohesion promoting agents include colloidal silicone dioxide, zinc oxide, polyvinylpyrrolidine, acrylate copolymers, crosspovidone, ethyl cellulose, acrylic copolymers, bentonites, clays, and mixtures thereof. In preferred embodiments, the cohesive promoting agent is colloidal silicon dioxide.

The amount of cohesion promoting agent present in the adhesive layer ranges from about 0% to about 15% by weight of the adhesive material, preferably ranging from about 3% to about 10% by weight of the adhesive material, most preferably ranging from about 5% to about 8% by weight of the adhesive material. In embodiments containing more than one adhesive layer, the amounts and/or types of cohesive promoting agent may be the same or different for each adhesive layer.

Non-limiting examples of penetration enhancers include methyl laurate, ethyl oleate, glycerol mono oleate, oleic acid, oleyl alcohol, isopropyl palmitate, isopropyl myristate, octyldodecanol, ω-pendadecalactone, cyclopendadecanone, propylene glycol monolaurate, eucalyptol, Ceraphyl 31, 1-dodecanol, transcutol P, triacetin, propylene glycol, dipropylene glycol, butylene glycol, ethanol, octanol, limonene, sorbitan monooleate, n-alkylphenol ether ethoxylates, n-alkyl ether ethoxylates, and mixtures thereof.

The amount of penetration enhancers present in the adhesive layer ranges from about 0% to about 40% by weight of the adhesive material, preferably ranging from about 0% to about 30% by weight of the adhesive material, most preferably ranging from about 0% to about 20% by weight of the adhesive material. In embodiments containing more than one adhesive layer, the amounts and/or types of penetration enhancers may be the same or different for each adhesive layer.

Non-limiting examples of plasticizers include mineral oil, silicone fluid, and mixtures thereof.

The amount of plasticizers present in the adhesive layer ranges from about 0% to about 40% by weight of the adhesive material, preferably ranging from about 0% to about 30% by weight of the adhesive material, most preferably ranging from about 0% to about 20% by weight of the adhesive material. In embodiments containing more than one adhesive layer, the amounts and/or types of plasticizer may be the same or different for each adhesive layer.

Non-limiting examples of tackifiers include silicone fluid, mineral oil, polybutenes, and mixtures thereof.

The amount of tackifier present in the adhesive layer ranges from about 0% to about 40% by weight of the adhesive material, preferably ranging from about 0% to about 30% by weight of the adhesive material, most preferably ranging from about 0% to about 10% by weight of the adhesive material. In embodiments containing more than one adhesive layer, the amounts and/or types of tackifier may be the same or different for each adhesive layer.

The inner-most layer of these solid dispersion transdermal delivery devices is the protective release liner, 13, 24, or 35. This layer is situated adjacent to the side of the adhesive layer, away from the backing layer. Prior to application and use of the solid dispersion transdermal delivery device, the protective release liner is peeled away from the adhesive layer/skin contact layer, 12, 23, or 34 and discarded. It provides a barrier to drug migration prior to the application of the device and is easily removable from the adhesive layer. The composition of the protective release liner is not critical. Any well-known release liner layer which possesses these qualities can be used in the present invention. Typically, the release liner comprises a base film coated with silicone or fluoropolymer which is thermally cured or cured with ultraviolet light in the presence of a photoinitiator/catalyst.

In a three-layer solid transdermal delivery device as depicted in FIG. 1, only one adhesive layer, a drug reservoir adhesive layer 12, is present and located between a backing layer 11 and a protective release liner 13. In such embodiments, it is the drug reservoir adhesive layer 12 which contacts and adheres to the skin subsequent to the removal of the release liner 13 and application of the device.

In a four-layer solid transdermal delivery device as depicted in FIG. 2, both a drug reservoir adhesive layer 22 and a skin contact adhesive layer 23 are present and adjacent to each other. The drug reservoir adhesive layer 22 is located between the backing layer 21 and the skin contact adhesive layer 23, while the skin contact adhesive layer 23 is located between the drug reservoir adhesive layer 22 and the protective release liner 24. In such embodiments, the skin contact adhesive layer 23 contacts and adheres to the skin subsequent to the removal of the release liner 24 and application of the device.

In a five-layer solid transdermal delivery device as depicted in FIG. 3, both a drug reservoir adhesive layer 32 and a skin contact adhesive layer 34 are present, but separated by a membrane layer 33. The drug reservoir adhesive layer is located between the backing layer 31 and the membrane layer 33, while the skin contact adhesive layer is located between the membrane layer 33 and the release liner 35. In such embodiments, the skin contact adhesive layer 34 contacts and adheres to the skin subsequent to the removal of the release liner 35 and application of the device.

As in a five-layer solid transdermal delivery device, embodiments containing two adhesive layers may further comprise a membrane, woven mesh or non woven 33. The membrane 33 is located between the drug reservoir adhesive layer 32 and the skin contact adhesive layer 34. The membrane layer may serve a variety of purposes, such as controlling diffusion and providing controlled release of the active pharmaceutical ingredient(s). The membrane layer is selected such that it is rate controlling, i.e., the presence of the membrane layer in the device may change the skin penetration profile of the device compared to a like device not having the membrane. The membrane, woven mesh or non woven may also serve as an anchorage layer between the two adhesive layers to reduce adhesive transfer.

Suitable membranes include continuous film membranes and microporous membranes and may be of woven or non-woven material. The membrane is preferably made of a flexible, polymeric material used conventionally by those skilled in the art. Polymer films which may be used for making the membrane layer include, without limitation, those comprising low density polyethylene, high density polyethylene, ethyl vinyl acetate copolymers, polypropylene and other suitable polymers. In one embodiment, the membrane layer is a microporous film membrane prepared from ethylene:vinyl acetate copolymers containing from about 0.5 to about 28 wt. % vinyl acetate. Suitable woven meshes include Saatifil® PES such as PES 105/52 available from Saatitech, Inc. A suitable non woven is Sontara® from DuPont Nonwovens Sontara Technologies.

In a preferred embodiment, the membrane layer is a microporous polypropylene membrane, such as Celgard® 2400 (available from Celgard, Inc., Solupor; Cotran 9702, Cotran 9705, Cotran 9706, Cotran 9707, Cotran 9712 Cotran 9715, Cotran 9716, Cotran 9728 (available from 3M™), and Solupor® 10P05A (available from DSM SoluTech). The membrane thickness can generally range from about 10 μm to about 100 μm, preferably the thickness can range from about 15 μm to about 50 μm.

The present invention also relates to methods of manufacturing the solid transdermal delivery devices described herein.

One embodiment is directed to a method of making a three-layered transdermal device 10 comprising a backing layer 11, an adhesive layer 12 comprising a therapeutic agent in amorphous form and a stabilizing agent with a hydrogen bond-forming functional group capable of hydrogen bonding with the therapeutic agent, and a protective release liner 13. First, a drug reservoir adhesive layer is prepared by completely dissolving both the therapeutic agent and the polymeric stabilizer in a solvent to form a uniform solution and mixing the solution with an adhesive or adhesive solution to form a new solution or suspension and then coating a release liner with the solution or suspension. The solution or suspension may also contain optional ingredients such as a penetration enhancer. The coated release liner is then dried to form a dry adhesive. The dry adhesive is then laminated to a backing film to form the three-layered film. Individual devices (or patches) containing the three layers are die-cut from the laminate. Traditional methods known in the art can be used to die-cut the layers from the laminate. Another embodiment is directed to a method of manufacturing a transdermal drug delivery device comprising a) mixing a first uniform solution comprising a first therapeutic agent in amorphous form and a first combination polymeric stabilizing and dispersing agent comprising a hydrogen bond-forming functional group with (ii) a first adhesive or adhesive solution to form a second solution or suspension, (b) coating a release liner with the second solution or suspension to form a first coated release liner, and (c) drying the first coated release liner.

In another embodiment is a method of making a four-layered transdermal device 20 comprising a drug reservoir layer 22, and a skin contact layer 23, each comprising a therapeutic agent in amorphous form and a stabilizing agent with a hydrogen bond-forming functional group capable of hydrogen bonding with the therapeutic agent, a backing layer 21, and a protective release liner 24. First, a drug reservoir adhesive layer on a release liner is prepared. A drug reservoir adhesive layer is prepared by completely dissolving both the therapeutic agent and the polymeric stabilizer in a solvent to form a uniform solution and mixing the solution with an adhesive or adhesive solution to form a new solution or suspension and then coating a release liner with the solution or suspension. The solution or suspension may also contain optional ingredients such as a penetration enhancer. The coated release liner is then dried to form a dry adhesive. The dry adhesive is then laminated to a backing film to form the three-layered film.

Second, a skin contact adhesive layer on a release liner is prepared. A skin contact adhesive layer is prepared by completely dissolving both the therapeutic agent and the polymeric stabilizer in a solvent to form a uniform solution and mixing the solution with an adhesive or adhesive solution to form a new solution or suspension and then coating a release liner with the solution or suspension. The solution or suspension may also contain optional ingredients such as a penetration enhancer. The coated release liner is then dried to form a dry adhesive.

Finally, to form the four-layer laminate, the available sides of the skin contact adhesive layer and drug reservoir layer are laminated together. Individual devices (or patches) containing the four layers are die-cut from the laminate. Traditional methods known in the art can be used to die-cut the layers from the laminate.

Another embodiment comprises a method of manufacturing a transdermal drug delivery device comprising: (a) mixing (i) a first uniform solution comprising a first therapeutic agent in amorphous form and a first combination polymeric stabilizing and dispersing agent comprising a hydrogen bond-forming functional group with (ii) a first adhesive or adhesive solution to form a second solution or suspension, (b) coating a release liner with the second solution or suspension to form a first coated release liner, and (c) drying the first coated release liner.

In another embodiment is a method of making a five-layered transdermal device 30 comprising a drug reservoir layer 32, and a skin contact layer 34, each comprising a therapeutic agent in amorphous form and a stabilizing agent with a hydrogen bond-forming functional group capable of hydrogen bonding with the therapeutic agent, a membrane 33 sandwiched between the drug reservoir layer 32 and skin contact layer 34, a backing layer 31, and a protective release liner 35. First, a drug reservoir adhesive layer on a release liner is prepared. A drug reservoir adhesive layer is prepared by completely dissolving both the therapeutic agent and the polymeric stabilizer in a solvent to form a uniform solution and mixing the solution with an adhesive or adhesive solution to form a new solution or suspension and then coating a release liner with the solution or suspension. The solution or suspension may contain a skin penetration enhancer. The coated release liner is then dried to form a dry adhesive. The dry adhesive is then laminated to a backing film to form the three-layered film. The release liner is then peeled off leaving a drug reservoir adhesive layer on a backing film.

In another embodiment is a method of manufacturing a transdermal drug delivery device comprises: (a) mixing (i) a first uniform solution comprising a first therapeutic agent in amorphous form and a first combination polymeric stabilizing and dispersing agent comprising a hydrogen bond-forming functional group with (ii) a first adhesive or adhesive solution to form a second solution or suspension, (b) coating a release liner with the second solution or suspension to form a first coated release liner, and (c) drying the first coated release liner. This method further comprises: (a') mixing (i) a second uniform solution comprising a second therapeutic agent in amorphous form, which may be the same as or different from the first therapeutic agent, and a second combination polymeric stabilizing and dispersing agent, which may be the same as or different from the first combination stabilizing and dispersing agent, comprising a hydrogen bond-forming functional group with (ii) a second adhesive or adhesive solution, which may be the same as or different from the first adhesive or adhesive solution, to form a third solution or suspension, (b') coating a second release liner, which may be the same as or different from the first release liner, with the third solution or suspension, (c') drying the coated second release liner, (d) laminating the first dried coated release liner onto one side of a membrane, woven mesh, or non-woven mesh, and (e) laminating the second dried coated release liner onto the second side of the membrane, woven mesh, or non-woven mesh.

The skin contact adhesive layer and drug reservoir layer can be simultaneously laminated to the membrane, woven mesh, or non woven. For this simultaneous lamination, the skin contact adhesive layer is first prepared by completely dissolving both the therapeutic agent and the polymeric stabilizer in a solvent to form a uniform solution. This solution is mixed with an adhesive or adhesive solution to form a new solution or suspension. The solution or suspension may also contain optional components such as a penetration enhancer. The solution or suspension is then coated onto the release liner. The coated release liner is then dried to form a dry adhesive. A membrane, woven mesh, or non woven is then laminated to the available side of the skin contact adhesive layer and at the same time, the drug reservoir adhesive layer is laminated to the other side of the membrane, woven mesh, or non woven to form a five layer laminate. Individual devices (or patches) containing five layers are die-cut from the laminate.

For non-simultaneous lamination, a laminate having a membrane, a skin contact adhesive layer, and a release liner is prepared. The skin contact adhesive layer is prepared by completely dissolving both the therapeutic agent and the polymeric stabilizer in a solvent to form a uniform solution. This solution is mixed with an adhesive or adhesive solution to form a new solution or suspension. The solution or suspension may also contain optional components such as a penetration enhancer. The solution or suspension is then coated onto the release liner. The coated release liner is then dried to form a dry adhesive. A membrane is then laminated to the available side of the skin contact adhesive layer. Finally, to form the five-layer laminate, the available side of the membrane from the skin contact adhesive laminate is laminated to the available side of the drug reservoir adhesive layer. Individual devices (or patches) containing five layers are die-cut from the laminate. Traditional methods known in the art can be used to die-cut the layers from the laminate.

In carrying out the procedures of the present invention, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

The entire disclosures of all applications, patents and publications, cited above and below, are hereby incorporated by reference in their entirety.

The following examples further illustrate the invention and its unique characteristics. These examples are not intended to limit the invention in any manner.

EXAMPLES

Examples 1 to 9

Solid dispersion of scopolamine transdermal system containing a stable amorphous form of scopolamine and a polymeric dispersant and stabilizer capable of forming hydrogen bond with scopolamine.

Example 1

To a glass jar Plastone 29/32 (12 g) and ethanol (7.56 g) were added. The admixture was mixed with a spatula, heated and sonicated in a water bath at 45° C. until a viscous solution was formed. To the solution was added scopolamine base (4.00 g). The admixture was mixed with a spatula, heated, sonicated and swirled until a clear viscous solution was formed. After the solution was cooled for a while, Dow Corning silicone adhesive 7-4302 (40.82 g, 60% solid) and ethyl acetate (8.34 g) were added. The material was quickly mixed at high shear to provide a cream-like uniform suspension. After air bubbles were removed by rolling overnight, the suspension was coated to a release liner, dried at room temperature for 5 minutes, in an oven set at 40° C. for 5 minutes and in an oven set at 85° C. for 5 minutes to form a thin layer of adhesive on release liner. A backing film Mediflex® 1502 was laminated to the adhesive side. Individual patches were die-cut and pouched. The resulting adhesive layer between the backing and release liner was opaque, free of scopolamine crystals as observed by microscopic analysis. DSC analysis of die-cut patches indicated the scopolamine was in amorphous form dispersed within the Plastone (PVP) matrix which was dispersed within the silicone adhesive matrix. The dispersed amorphous scopolamine in the patch had a glass transition temperature (Tg) of 29° C. The glass transition temperature of undispersed amorphous scopolamine is about 10° C. The higher glass transition temperature of the dispersed amorphous scopolamine is the result of the intermolecular interactions between the dispersant PVP and scopolamine molecules including hydrogen bonding. X-ray diffraction indicated scopolamine was in amorphous form in the patch. The in vitro flux study indicated 211 µg/cm$^2$ was delivered within 72 hours. The flux of this solid transdermal system containing stable amorphous form of scopolamine is much higher than the flux of a crystalline scopolamine formulation (88 µg/cm$^2$).

Individual pouched patches were stored at 40° C. and room temperature. After 8 months at 40° C. or 19 months at room temperature, no crystals were observed by microscopic and DSC and X-ray powder diffraction analyses, indicating scopolamine remained in amorphous form in the patch.

TABLE 1

Solid dispersion scopolamine transdermal system summary

| Ex. No. | Composition | PVP/ scop ratio | In vitro flux at 72 hr., µg/cm$^2$ | Presence of crystals | Completely present as Amorphous form, time 0 | Completely present in dispersed amorphous form in aged sample | | | |
|---|---|---|---|---|---|---|---|---|---|
| | | | | | | 8 month at 40° C. | 19 month at RT | 6 month at 40° C. | 6 month at RT |
| 1 | 10% scop, 30% PVP, 60% silicone adhesive | 3 to 1 | 211 | No | Yes | Yes | Yes | Yes | Yes |
| 2 | 10% scop, 20% PVP, 70% silicone adhesive | 2 to 1 | 463 | No | Yes | Yes | Yes | Yes | Yes |
| 3 | 5% scop, 10% PVP, 80% silicone adhesive, 5% silicone fluid | 2 to 1 | 295 | No | Yes | | | Yes | Yes |
| 4 | 4% scop, 8% PVP, 88% silicone adhesive | 2 to 1 | 249 | No | Yes | | | Yes | Yes |
| 5 | 4% scop, 8% PVP, 83% silicone adhesive, 5% silicone fluid | 2 to 1 | 213 | No | Yes | | | Yes | Yes |

TABLE 1-continued

Solid dispersion scopolamine transdermal system summary

| Ex. No. | Composition | PVP/ scop ratio | In vitro flux at 72 hr., μg/cm² | Presence of crystals | Completely present as Amorphous form, time 0 | Completely present in dispersed amorphous form in aged sample | | | |
|---|---|---|---|---|---|---|---|---|---|
| | | | | | | 8 month at 40° C. | 19 month at RT | 6 month at 40° C. | 6 month at RT |
| 6 | 6% scop, 12% PVP, 82% silicone adhesive | 2 to 1 | 271 | No | Yes | | | Yes | Yes |
| 7 | 6% scop, 12% PVP, 77% silicone adhesive, 5% silicone fluid | 2 to 1 | 251 | No | Yes | | | Yes | Yes |
| 8 | 5% scop, 10% PVP, 85% silicone adhesive | 2 to 1 | 307 | No | Yes | | | Yes | Yes |
| 9 | 6% scop, 12% PVP, 79% silicone adhesive, 3% silicone fluid | 2 to 1 | 627 | No | Yes | | | Yes | Yes |

The data in Table 1 indicates a weight ratio of PVP to scopolamine of 2 to 1 is sufficient to stabilize the dispersed scopolamine amorphous form for a long period of time.

Example 10 to 15

Solid dispersion of natrexone transdermal system containing a stable amorphous form of naltrexone and a polymeric dispersant and stabilizer capable of forming hydrogen bond with naltrexone. The data in Table 2 indicates that naltrexone whose amorphous form has a higher glass transition temperature (79.5° C.) than the glass transition temperature of amorphous scopolamine requires less PVP to disperse and stabilize it. The solid dispersion transdermal systems have higher flux than the crystalline suspension transdermal system example 15.

The data in Table 2 indicates a weight ratio of PVP to naltrexone of 1 to 1 is sufficient to stabilize the dispersed naltrexone amorphous form for a long period of time.

I claim:

1. A transdermal drug delivery device comprising:
   (a) a backing film;
   (b) a first adhesive layer comprising a solid dispersion, said dispersion comprising: a first adhesive, a first therapeutic agent in amorphous form, and a first combination polymeric stabilizing and dispersing agent comprising a hydrogen bond-forming functional group; and
   (c) a protective release liner; wherein
   the first therapeutic agent has a glass transition temperature of at least 70° C., and the weight ratio of the polymeric stabilizing and dispersing agent to the first therapeutic agent in amorphous form is between 0.5 and 2; or

TABLE 2

Solid dispersion naltrexone transdermal system summary

| Ex. No. | Composition | PVP/ NTX ratio | In vitro flux at 168 hr., μg/cm² | Presence of crystals | Completely present as Amorphous form time 0? | Completely present in dispersed Amorphous form in aged sample - 1 month |
|---|---|---|---|---|---|---|
| 10 | 15% NTX, 20% PVP, 65% silicone 7-4302 | 1.3 to 1 | 488 | No | Yes | Yes |
| 11 | 10% NTX, 10% PVP, 80% silicone 7-4301 | 1 to 1 | 279 | No | Yes | Yes |
| 12 | 10% NTX, 10% PVP, 45% silicone 7-4302, 35% dodecanol | 1 to 1 | 1185 | No | Yes | Yes |
| 13 | 15% NTX, 15% PVP, 35% silicone 7-4302, 35% dodecanol | 1 to 1 | 1297 | No | Yes | Yes |
| 14 | 20% NTX, 20% PVP, 35% acrylic 87-2979, 25% dodecanol | 1 to 1 | 669 | No | Yes | Yes |
| 15 | 15% NTX, 85% acrylic 87-2979 | 0 to 1 | 106 | Yes | No | No | the first therapeutic agent has a glass transition temperature of less than 40° C., and the weight ratio of the polymeric stabilizing and dispersing agent to the first therapeutic agent in amorphous form is between 2 and 10;

wherein the first therapeutic agent is scopolamine or naltrexone; and wherein the first therapeutic agent in amorphous form is 10% to 20% of the solid dispersion by weight of each.

2. The drug delivery device of claim 1, wherein at least 95% of the first therapeutic agent is in amorphous form after storage at room temperature for at least six months.

3. The drug delivery device of claim 2, wherein at least 99% of said therapeutic agent is in amorphous form after storage at room temperature for at least six months.

4. The drug delivery device of claim 3, wherein at least 99% of said therapeutic agent is in amorphous form after storage at room temperature for at least 18 months.

5. The drug delivery device of claim 1, wherein said therapeutic agent has a skin absorption rate which is increased by at least 50% compared to the skin absorption rate of said therapeutic agent in an identical transdermal drug delivery without said polymeric stabilizing and dispersing agent.

6. The transdermal drug delivery device of claim 1, further comprising (d) a second adhesive layer between said first adhesive layer and said protective release liner, said second adhesive layer comprising: a second adhesive which may be the same as or different from said first adhesive, a second therapeutic agent in amorphous form which may be the same as or different from said first therapeutic agent, and a second combination polymeric stabilizing and dispersing agent which may be the same as or different from said first combination polymeric stabilizing and dispersing agent, said agent comprising a hydrogen bond-forming functional group, wherein the second therapeutic agent has a glass transition temperature of at least 70° C., and the weight ratio of the second polymeric stabilizing and dispersing agent to the second therapeutic agent is between 0.5 and 2, or the second therapeutic agent has a glass transition temperature of less than 40° C., and the weight ratio of the second polymeric stabilizing and dispersing agent to the second therapeutic agent is between 2 and 10; and wherein the second therapeutic agent in amorphous form is 10% to 20% of the second adhesive layer by weight of each.

7. The drug delivery device of claim 6, further comprising: (e) a membrane between said first and second adhesive layers.

8. The drug delivery device of claim 1, wherein said first adhesive layer further comprises a member selected from the group consisting of a skin penetration enhancer, a tackifier, a cohesive promoter, and any combination of any of the foregoing.

9. The drug delivery device of claim 6, wherein said first, second, or both first and second adhesive layers independently further comprise a member selected from the group consisting of a skin penetration enhancer, a tackifier, a cohesive promoter, and any combination of any of the foregoing.

10. The drug delivery device of claim 1, wherein said therapeutic agent in amorphous form contains at least one hydrogen bond-forming group.

11. The drug delivery device of claim 10, wherein there is one or more hydrogen bonds between said therapeutic agent in amorphous form and said polymeric stabilizing and dispersing agent and wherein said drug delivery device has greater dispersion capability compared to an identical transdermal drug delivery device without said polymeric stabilizing and dispersing agent.

12. The drug delivery device of claim 1, wherein the first therapeutic agent in amorphous form contains less than 1.0% crystallinity.

13. The drug delivery device of claim 1, wherein said adhesive is selected from the group consisting of a polysiloxane, polyisobutylene, an acrylic adhesive, or any combination of any of the foregoing.

14. A method of manufacturing a transdermal drug delivery device, said method comprising: (a) mixing (i) a first uniform solution comprising a first therapeutic agent in amorphous form and a first combination polymeric stabilizing and dispersing agent comprising a hydrogen bond-forming functional group with (ii) a first adhesive or adhesive solution to form a second solution or suspension, (b) coating a release liner with said second solution or suspension to form a first coated release liner, and (c) drying said first coated release liner; wherein the therapeutic agent has a glass transition temperature of at least 70° C., and the weight ratio of the polymeric stabilizing and dispersing agent to the first therapeutic agent in amorphous form is between 0.5 and 2; or the therapeutic agent has a glass transition temperature of less than 40° C., and the weight ratio of the polymeric stabilizing and dispersing agent to the therapeutic agent is between 2 and 10;

wherein the first therapeutic agent is scopolamine or naltrexone, and wherein the first therapeutic agent in amorphous form is 10% to 20% of the second solution or suspension by dry weight of each.

15. The method of claim 14, further comprising the step of: (d) laminating the dry coated release liner onto a backing film.

16. The method of claim 14, further comprising the step of: (e) die-cutting one or more unit dosage forms from the laminate.

17. The method of claim 14, wherein one or more of said uniform solution, first adhesive, adhesive solution, second solution or suspension independently further comprises a member selected from the group consisting of a skin penetration enhancer, a tackifier, a cohesive promoter, or a combination of any of the foregoing.

18. The method of claim 14, further comprising (a') mixing (i) a third uniform solution comprising a second therapeutic agent in amorphous form, which may be the same as or different from said first therapeutic agent, and a second combination polymeric stabilizing and dispersing agent, which may be the same as or different from said first combination stabilizing and dispersing agent comprising a hydrogen bond-forming functional group with (ii) a second adhesive or adhesive solution, which may be the same as or different from said first adhesive or adhesive solution, to form a fourth solution or suspension, (b') coating a second release liner, which may be the same as or different from said first release liner, with said fourth solution or suspension, (c') drying the coated second release liner, (d) laminating the first dried coated release liner onto a backing film, (e) removing said first release liner from said first coated release liner to form a first dried coating layer, and (f) laminating the second dried coated release liner to said first dried coating layer, wherein the second therapeutic agent has a glass transition temperature of at least 70° C., and the weight ratio of the second polymeric stabilizing and dispersing agent to the second therapeutic agent is between 0.5 and 2, or the second therapeutic agent has a glass transition temperature of less than 40° C., and the weight ratio of the second polymeric stabilizing and dispersing agent to the second therapeutic agent is between 2 and 10; and wherein the second therapeutic agent in amorphous form is 10% to 20% of the fourth solution or suspension by dry weight of each.

19. The method of claim 18, wherein one or more of said first uniform solution, first adhesive or adhesive solution, second solution or suspension, third uniform solution, second adhesive or adhesive solution, or fourth solution or suspension independently further comprises a member selected from the group consisting of a skin penetration enhancer, a tackifier, a cohesive promoter, and any combination of any of the foregoing.

20. The method of claim 14, further comprising: (a') mixing (i) a third uniform solution comprising a second therapeutic agent in amorphous form, which may be the same as or different from said first therapeutic agent, and a second combination polymeric stabilizing and dispersing agent, which may be the same as or different from said first combination stabilizing and dispersing agent, comprising a hydrogen bond-forming functional group with (ii) a second adhesive or adhesive solution, which may be the same as or different from said first adhesive or adhesive solution, to form a fourth solution or suspension, (b') coating a second release liner, which may be the same as or different from said first release liner, with said fourth solution or suspension, (c') drying the coated second release liner, (d) laminating the first dried coated release liner onto one side of a membrane, woven mesh, or non-woven mesh, and (e) laminating the second dried coated release liner onto the second side of said membrane, woven mesh, or non-woven mesh, wherein the second therapeutic agent has a glass transition temperature of at least 70° C., and the weight ratio of the second polymeric stabilizing and dispersing agent to the second therapeutic agent is between 0.5 and 2, or the second therapeutic agent has a glass transition temperature of less than 40° C., and the weight ratio of the second polymeric stabilizing and dispersing agent to the second therapeutic agent is between 2 and 10; and wherein the second therapeutic agent in amorphous form is 10% to 20% of the fourth solution or suspension by dry weight of each.

21. The method of claim 20, wherein steps (d) and (e) occur simultaneously.

22. The method of claim 20, wherein step (d) occurs before step (e).

23. The method of claim 20, wherein one or more of said first uniform solution, first adhesive or adhesive solution, second solution or suspension, second uniform solution, second adhesive or adhesive solution, or third solution or suspension independently further comprises a member selected from the group consisting of a skin penetration enhancer, a tackifier, a cohesive promoter, and any combination of any of the foregoing.

24. The drug delivery device of claim 1, wherein the polymeric stabilizing and dispersing agent is selected from polyvinylpyrrolidone, poly(vinylpyrrolidone-vinylacetate) copolymer, hydroxypropyl cellulose, hydroxypropyl methyl cellulose, hydroxyethyl cellulose, ethylcellulose, or a combination thereof.

25. The drug delivery device of claim 6, wherein the second therapeutic agent in amorphous form are independently selected from the group consisting of scopolamine, oxybutynin, naltrexone, testosterone, estradiol, rotigotine, fentanyl, ethinyl estradiol, norelgestral, and pharmaceutically acceptable salts thereof.

* * * * *